United States Patent [19]

Strecker et al.

[11] Patent Number: 5,539,134
[45] Date of Patent: Jul. 23, 1996

[54] PROCESS FOR THE PREPARATION OF N-ALKANOYL-POLYHYDROXYALKYLAMINES

[75] Inventors: Beate Strecker, Ludwigshafen; Helmut Wolf, Hassloch; Gerhard Wolf, Ketsch; Alfred Oftring, Bad Durkheim; Hans-Heinrich Bechtolsheimer, Dittelsheim-Hessloch; Dieter Hertel, Leimen, all of Germany

[73] Assignee: BASF Aktiengesellschaft, Ludwigshafen, Germany

[21] Appl. No.: 325,182

[22] PCT Filed: Oct. 15, 1993

[86] PCT No.: PCT/EP93/02852

§ 371 Date: Apr. 24, 1995

§ 102(e) Date: Apr. 24, 1995

[87] PCT Pub. No.: WO94/10130

PCT Pub. Date: May 11, 1994

[30] Foreign Application Priority Data

Oct. 23, 1992 [DE] Germany .................. 42 35 783.7

[51] Int. Cl.⁶ .................................................. C07C 231/00
[52] U.S. Cl. .................. 554/69; 554/66; 554/68
[58] Field of Search ..................... 554/66, 68, 69

[56] References Cited

U.S. PATENT DOCUMENTS 5,338,487  8/1994  Conner et al. ................. 554/66

FOREIGN PATENT DOCUMENTS

WO92/06071  4/1992  WIPO.

*Primary Examiner*—José G. Dees
*Assistant Examiner*—Deborah D. Carr
*Attorney, Agent, or Firm*—Oblon, spivak, McClelland, Maier, & Neustadt

[57] ABSTRACT

The preparation von N-alkanoyl-polyhydroxyalkylamines I in which $$Z-N(R^1)-C(=O)-R^2 \quad (I)$$

in which

Z stands for the polyhydroxyalkyl radical of a monosaccharide or oligosaccharide, $R^1$ denotes hydrogen or $C_1-C_8$ alkyl and $R^2$ denotes $C_1-C_{21}$ alkyl, by the reaction of polyhydroxyalkylamines of the general formula II $$Z-NH-R^1 \quad (II),$$

with alkyl carboxylates of the general formula III $$R^3-O-C(=O)-R^2 \quad (III)$$

in which $R^3$ denotes a $C_1-C_4$ alkyl radical, in the presence of a basic catalyst, in which (a) all of the ester III is placed in the reactor and is heated to the reaction temperature, and the amine II is metered in in the form of a melt while the reaction proceeds, while alcohol $R^3$—OH formed is continuously removed by distillation, (b) the reaction is carried out at a temperature of from 55° to 110° C., and (c) the reaction is carried out in the absence of organic solvents.

5 Claims, No Drawings

PROCESS FOR THE PREPARATION OF N-ALKANOYL-POLYHYDROXYALKYLAMINES

This application is a 371 of PCT1/EP93/02852.

BACKGROUND OF THE INVENTION

1. Field of the Invention

The present invention relates to an improved process for the preparation of N-alkanoyl-polyhydroxyalkylamines by the reaction of polyhydroxyalkylamines with alkyl carboxylates in the presence of a basic catalyst.

2. Discussion of the Background

N-alkanoyl-polyhydroxyalkylamines, which are mainly used as surface-active agents in detergent and cleaner formulations, have been known in the art for many years and are frequently prepared from the aforementioned starting materials.

Thus U.S. Pat. No. 2,703,798 (1) teaches the reaction of N-monoalkylglucamines with aliphatic esters of fatty acids at temperatures of from 140° to 230° C.; in this method, the components are placed together in the reaction vessel before the reaction is started by heating.

EP-A 285,768 (2) reveals that the reaction of fatty acids or fatty acid esters with optionally N-substituted polyhydroxyalkylamines can be carried out in the melt, optionally in the presence of alkaline catalysts; a typical example is the preparation of N-methyl coconut fatty acid glucamide from the methyl ester of coconut fatty acid and N-methylglucamine by adding sodium methylate and heating the two components to 135° C.

WO 92/06,071 (3) relates to a process for the manufacture of surface-active linear glucamides from N-alkylglucamines and fatty acid esters in which certain phase-transfer catalysts are added; first of all, a two-phase mixture is prepared by heating and intermixing the two components, and the reaction is then started by the addition of the catalyst and is subsequently carried out at temperatures of from 120° to 200° C.

WO 92/06,073 (4) reveals that it is possible to prepare polyhydroxy fatty acid amides from N-alkyl-polyhydroxyamines and fatty acid esters in a hydroxyl group-containing or alkoxylated solvent such as methanol, propylene glycol or an ethoxylated alcohol in the presence of a basic catalyst at temperatures of from 40° to 100° C.

A disadvantage of the prior art processes is that the product obtained usually contains a high proportion of starting material and by-products; this particularly applies to the processes disclosed in (1) to (3). When use is made of organic solvents as described in (4) these must be removed from the reaction mixture, on completion of the reaction, in an uneconomical manner, ie, by distillation; in addition to the extra energy costs incurred by separation there may also ensue environmental problems connected with the purification or disposal of these solvents.

Another disadvantage of the prior art processes is frequently the tendency of the reaction mixture to form lumps or to stick to the walls of the reactor, which makes it more difficult to maintain the reaction conditions and thus to reproduce the properties of the product and also entails problems concerning cleaning of the reactor.

It is thus an object of the present invention to overcome the above drawbacks of the prior art.

DETAILED DESCRIPTION OF THE PREFERRED EMBODIMENTS

Accordingly, we have found a process for the preparation of N-alkanoyl-polyhydroxyalklamines of the general formula I

in which z stands for the polyhydroxyalkyl radical of a monosaccharide or oligosaccharide, $R^1$ denotes hydrogen or $C_1$–$C_8$ alkyl and $R^2$ denotes $C_1$–$C_{21}$ alkyl, by the reaction of polyhydroxyalkylamines of the general formula II

with alkyl carboxylates of the general formula III

in which $R^3$ denotes a $C_1$–$C_4$ alkyl radical, in the presence of a basic catalyst, wherein (a) all of the ester III is placed in the reactor and is heated to the reaction temperature, and the amine II is metered in in the form of a melt while the reaction proceeds, whilst alcohol $R^3$—OH formed is continuously removed by distillation, (b) the reaction is carried out at a temperature of from 55° to 110° C., and (c) the reaction is carried out in the absence of organic solvents, except when these organic solvents assume the function of dispersing agents.

The process of the invention is carried out in accordance with proviso (a) as follows: the total amount of the ester III is placed in a reactor and is heated to the temperature required for the reaction. Thereafter the amine II is metered in portionwise or preferably continuously at such a rate that the temperature in the reactor remains constant or at least stays within the limits stated in proviso (b).

The amine II is metered in as a melt, whose temperature can be above that of the reaction mixture in the reactor. The amine II used need not be specially purified for this purpose and the commercial mixtures produced in the reductive amination of sugar derivatives can be used. However, these starting materials must be sufficiently anhydrous and the water content should be less than 1 wt. % and is preferably less than 0.5 wt. %. To achieve this end, commercial materials can be dehydrated by usual methods.

It is also possible, theoretically, to add the amine II as solid substance via suitable means for metering solids, but this necessitates rather extensive engineering measures and is thus of less economical interest.

Alcohol $R^3$—OH formed during the reaction and small amounts of solvents possibly introduced with the basic catalyst or other auxiliaries are continuously removed by distillation. In order to facilitate this distillation process, it is recommendable to carry out the reaction under reduced pressure, for example at from 20 to 500 mbar and preferably from 30 to 300 mbar and more preferably from 50 to 150 mbar.

In accordance with proviso (b), the reaction is carried out at a temperature of from 55° to 110° C., preferably from 80° to 100° C. and more preferably from 80° to 100° C. The amine II and the ester III are used in an approximately equimolar ratio to each other, although a slight excess of one or other of the components of, say, The time usually taken for metering the amine II to the ester III is from 15 min to 4 h and especially from 30 min to 3 h. When all of the amine II has been added, stirring is frequently continued for a further 30 min to 3 h at the temperature stated, but there is no need for such further stirring when the reactants react speedily.

In accordance with proviso (c) the process of the invention is carried out in the absence of organic, especially polar organic, solvents. Alcohol formed during the reaction and any solvents introduced in small quantities by auxiliaries are immediately removed by distillation.

Since the process of the invention is carried out by slow addition of a melt of the amine II to the liquid ester III with rapid reaction thereof, there is present, at all times, a homogeneous, single-phase reaction mixture, which fact greatly simplifies the control of the reaction.

The polyhydroxyalkyl radical Z is derived from monosaccharides such as erythrose, threose, ribose, arabinose, xylose, lyxose, allose, altrose, glucose, mannose, gulose, idose, galactose, talose or fluctose or derivatives thereof such as glucuronic acid or deoxyribose or oligosaccharides and especially disaccharides such as saccharose, lactose, trehalose, maltose, cellobiose or gentiobiose, and also from trisaccharides such as raffinose. Also suitable are all commercial starch degradation products such as glucose syrup or dextrins, eg, maltodextrins.

A preferred value for the variable Z is a polyhydroxyalkyl radical derived from aldohexoses and having the formula $-CH_2-(CHOH)_4-CH_2OH$. Particularly preferred is the radical of glucose and especially of naturally occurring $D(+)$-glucose.

The amines II used as starting materials can be prepared in known manner simply by reductive amination of said sugars or sugar derivatives with ammonia or alkylamines $R_1-NH_2$.

The radical $R^1$ denotes hydrogen or $C_1-C_8$ alkyl such as methyl, ethyl, n-propyl, isopropyl, n-butyl, isobutyl, sec-butyl, tert-butyl, n-pentyl, n-hexyl, n-heptyl, n-octyl, or 2-ethylhexyl. Of these, $C_1-C_4$ alkyl is preferred and especially methyl, ethyl, n-propyl, and n-butyl.

The radical $R^2$ designates $C_1-C_{21}$ alkyl, preferably $C_2-C_{21}$ alkyl and more preferably $C_5-C_{19}$ alkyl, especially $C_7-C_{17}$ alkyl. $R^2$ preferably stands for the radical of a long-chain carboxylic acid and especially of a naturally occurring fatty acid such as lauric acid, myristic acid, palmitic acid or stearic acid or a carboxylic acid synthetically prepared by the Oxo or Ziegler methods. Also, mixtures of different radicals $R^2$ can be used.

The radical $R^3$ denotes $C_1-C_4$ alkyl such as methyl, ethyl, n-propyl, isopropyl, n-butyl, isobutyl, sec-butyl, or tert-butyl, of which methyl and ethyl are preferred.

Suitable basic catalysts are primarily alkali metal hydroxides such as sodium or potassium hydroxide, alkali metal carbonates such as sodium or potassium carbonate and alkali metal alcoholates such as sodium or potassium methanolate, sodium or potassium ethanolate or sodium or potassium propylate. The catalysts are added in the commonly used amounts, ie, approximately from 1 to 25 mol %, based on the starting compounds. The said catalysts can be added as solid substance or, in the case of the alcoholates, as approximately 10 to 40 wt. % strength and especially 20 to 30 wt. % strength solutions in the appropriate alcohols. The addition of the catalyst to the ester III is carried out either in a single portion prior to the addition of the amine II or, preferably, portionwise or continuously while the amine II is being metered to the ester III.

The reaction usually proceeds with less trouble and to a higher degree of completion when a conventional dispersing agent is added in commonly used concentrations. Examples of suitable compounds are propylene glycol or the product of the reaction itself, ie, an N-alkanoyl-polyhydroxyalkylamine I. However, particularly suitable substances for this purpose are those having themselves surface-active properties. Thus it is possible for the process of the invention to create mixtures of compounds I and other surfactants, and these mixtures can be directly used in, for example, detergent and cleaner applications.

Suitable surface-active dispersing agents of this type are, in particular, alkoxylates of $C_8-C_{20}$ alcohols, especially ethoxylates and propoxylates of usual fatty alcohols or oxo-alcohols containing from about 2 to about 15 alkylene oxide units.

The said dispersing agents are usually co-used in a concentration of from 10 to 300 wt. % and preferably from 20 to 200 wt. % of the weight of ester III used.

On completion of the reaction, the catalyst used is advantageously neutralized, for example with a weak organic acid such as citric acid.

The process of the invention may be carried out batchwise or continuously in, for example, a cascade of stirred boilers.

The process of the invention produces colorless or faintly colored products having a high content of I and a distinctly narrower spectrum of starting materials and by-products than the products of conventional prior art processes. The by-products which occur in said processes are usually cyclic N-alkanoyl-polyhydroxyalkylamines, resulting from intramolecular cyclization in the sugar moiety of the molecule I, and ester amides, resulting from the reaction of I with a further molecule of III with esterification taking place at a hydroxyl group in the sugar moiety of I.

The products produced by the process of the invention require no further purification for most applications. The high degree of purity and the selective formation of the N-alkanoyl-polyhydroxyalkylamines I mainly result from the fact that the reaction is carried out at temperatures well below the melting range of the amines II and the reaction product is thus subjected to a substantially smaller thermal load than is the case with most prior art processes.

A particular advantage of the process of the invention is that there exists a homogeneous phase of low viscosity throughout the reaction, which ensures that there is intimate mixing of the components at all times, that the reaction and its control are very simple to carry out, and that there is no formation of lumps in the mixture or incrustations on the walls of the reactor. For this reason, the process of the invention is also suitable for large-scale production of N-alkanoyl-polyhydroxyalkylamines I.

Another advantage of the process of the invention is the omission of organic solvents, which give rise to additional engineering and energy costs and frequently create environment problems.

Examples 1 to 4 and Comparative Example A

Preparation von N-lauroyI-N-methylglucamine

EXAMPLE 1

In a reactor there were placed 327 g (1.5 mol) of methyl laurate and 27 g of a 30 wt. % strength methanolic sodium methanolate solution (0.15 mol of $NaOCH_3$), and this mixture was heated to 80° C. Under reduced pressure (80 mbar), a melt having a temperature of 130° C. and composed of 293 g (1.5 mol) of N-methylglucamine and 54 g of propylene glycol was added dropwise over a period of 40 rain such that the temperature in the reactor remained at a constant level of 80° C. At the same time, the methanol formed during the reaction was continuously removed by distillation, in vacuo, together with the methanol added with the catalyst solution.

The reaction mixture was then stirred for a further 1 to 2 h at 80° C. and then neutralized with 14.1 g of citric acid. There was obtained a light-colored waxy product melting in the range of from 70° to 80° C.

EXAMPLE 2

27 g (1.5 mol) of methyl laurate were placed in a reactor together with 54 g of propylene glycol and heated to 80° C. Under reduced pressure (80 mbar), concurrently 293 g (1.5 mol) of molten N-methylglucamine having a temperature of 130° C. and 27 g of 30 wt. % strength methanolic sodium methanolate solution (0.15 mol Of NaOCH₃) were added dropwise over a period of 45 min whilst keeping the temperature constant at 80° C. The methanol added with the catalyst and that liberated during the reaction was continuously removed by distillation in vacuo. On completion of the reaction, stirring was continued for a further hour at 80° C. and the product was then neutralized with 9.4 g of citric acid. There was obtained a light-colored waxy product melting in the range of from 70° to 80° C.

EXAMPLE 3

219 g (1 mol) of methyl laurate were placed in a vessel together with 22 g of non-neutralized N-lauroyl-N-methylglucamine from Example 1 and the mixture was heated to 100° C. Under reduced pressure (80mbar), 195 g (1 mol) of molten N-methylglucamine having a temperature of 130° C. and 18 g of 30 wt. % strength methanolic sodium methanolate solution (0.1 mol of NaOCH₃) were metered in over a period of 35 rain whilst keeping the temperature constant at 100° C. The rest of the experiment was carried out as described in Example 2. There was obtained a pale yellow waxy product.

EXAMPLE 4

220 g (1 mol) of methyl laurate were placed in a reactor and heated to 100° C. Under reduced pressure (80mbar), 195 g (1 mol) of molten N-methylglucamine having a temperature of 130° C. and 18 g of 30 wt. % strength methanolic sodium methylate solution (0.1 mol of NaOCH₃) were concurrently added dropwise over a period of 45 min whilst keeping the temperature constant at 100° C. The methanol formed during the reaction was continuously removed by distillation in vacuo together with the methanol from the catalyst solution. When the addition was near completion, the viscosity of the reaction mixture rose considerably. After the methanol had been completely removed from the reaction mixture, the product was neutralized with 9.4 g of citric acid. There was obtained a brown-colored waxy product.

Comparative Example A 98 g (0.5 mol) of solid N-methylglucamine and 110 g (0.5 mol) of methyllaurate were placed in a reactor and melted at 125° C., 2 phases were formed. The mixture was then heated to 170° C. and stirred at this temperature for 1.5 h, The methanol formed during the reaction was removed by distillation. There was obtained a brown-colored clear melt.

The following table lists the composition of the products obtained. The analysis was carried out by gas chromatography, and the percentages are by area.

TABLE

| | Composition of the Products | | | | |
|---|---|---|---|---|---|
| Example | 1 | 2 | 3 | 4 | A |
| N-methylglucamine | 0.31 | 0.60 | 1.71 | 4.08 | 7.98 |
| (lauric acid)/(lauric ester) | 3.28 | 2.27 | 2.01 | 2.47 | 7.73 |
| lauryl glucamine linear | 93.04 | 95.60 | 92.18 | 91.06 | 60.72 |
| lauryl glucamine cyclic | 0.22 | 0.10 | 0.86 | 0.93 | 10.93 |
| ester amides and other by-products | 3.15 | 1.43 | 3.24 | 1.46 | 12.74 |

We claim:
1. A process for the preparation of N-alkanoyl-polyhydroxyalkylamines of the general formula I

in which

Z stands for the polyhydroxyalkyl radical of a monosaccharide or oligosaccharide, $R^1$ denotes hydrogen or $C_1$–$C_8$ alkyl and $R^2$ denotes $C_1$–$C_{21}$ alkyl, by the reaction of polyhydroxyalkylamines of the general formula II

with alkyl carboxylates of the general formula III

in which $R^3$ denotes a $C_1$–$C_4$ alkyl radical, in the presence of a basic catalyst, wherein (a) all of the ester III is placed in the reactor and is heated to the reaction temperature, and the amine II is metered in in the form of a melt at a rate sufficient to maintain a homogeneous, single phase-reaction mixture while the reaction proceeds, whilst alcohol $R^3$—OH formed is continuously removed by distillation, (b) the reaction is carried out at a temperature of from 55° to 110° C., and (c) the reaction is carried out in the absence of organic solvents, except when these organic solvents assume the function of dispersing agents.

2. A process as claimed in claim 1, wherein the variable Z stands for a polyhydroxyalkyl radical of the formula —$CH_2$—$(CHOH)_4$—$CH_2OH$.

3. A process as claimed in claim 1, wherein the radical $R^1$ denotes $C_1$–$C_4$ alkyl.

4. A process as claimed in claim 1, wherein the radical $R^2$ denotes $C_5$–$C_{19}$ alkyl.

5. A process as claimed in claim 1, wherein the reaction is carried out at a temperature of from 80° to 100° C.

* * * * *